United States Patent [19]

Nimni et al.

[11] 4,378,224
[45] Mar. 29, 1983

[54] COATING FOR BIOPROSTHETIC DEVICE AND METHOD OF MAKING SAME

[76] Inventors: Marcel E. Nimni, 2800 Neilson Way #908, Santa Monica, Calif. 90405; David T. Cheung, 147 N. Mission Dr., San Gabriel, Calif. 91775

[21] Appl. No.: 188,964

[22] Filed: Sep. 19, 1980

[51] Int. Cl.³ .................... C14C 3/16; C14C 3/16; C14C 15/00; B23Q 23/00
[52] U.S. Cl. ................................ 8/94.11; 8/404
[58] Field of Search .............. 8/94.11, 94.21, 404; 3/1.4, 1.5

[56] References Cited

U.S. PATENT DOCUMENTS

| 2,640,752 | 6/1953 | Davis | 8/94.11 |
|---|---|---|---|
| 2,938,892 | 5/1960 | Sheehan | 8/94.11 |
| 3,673,612 | 7/1972 | Merril et al. | 3/1 |
| 3,865,615 | 2/1975 | Manly | 3/1 |
| 3,908,201 | 9/1975 | Jones et al. | 3/1 |
| 3,966,401 | 6/1976 | Hancock et al. | 8/94.11 |
| 4,050,893 | 9/1977 | Hancock et al. | 8/94.11 |
| 4,077,069 | 3/1978 | Perkins | 3/1 |
| 4,082,507 | 4/1978 | Sawyer | 8/94.11 |
| 4,098,571 | 7/1978 | Miyata et al. | 8/94.11 |
| 4,120,649 | 10/1978 | Schechter | 3/1 |

FOREIGN PATENT DOCUMENTS 559701 7/1977 U.S.S.R. .................. 3/1.4

OTHER PUBLICATIONS

Sawyer et al., *Artificial Organs*, vol. 1, No. 2, Nov. 1977.
Ferrans et al., *The Amer. Jour. of Cardiology*, vol. 41, (1978), pp. 1159-1184.
Broom et al., *Thorax*, vol. 34, (1979), pp. 166-176.
Larsson et al., *Thrombosis and Haemostasis*, vol. 37, No. 2, pp. 261-273 (1977).
Strawich et al., *Biomat., Med. Dev. Art. Org.*, vol. 3, No. 3 (1975) pp. 309-318.
Cohen et al., *Cardiovascular Surgery*, Supp. 3, Circulation, vol. 54, No. 6, (1976), pp. III-60-63.
McIntosh et al., *Surgery*, vol. 78, No. 6 (1975), pp. 768-775.
Zudie et al., *The Annals of Thoracic Surgery*, vol. 17, #5, pp. 479-491 (1975).
Mattila et al., *Annals Chirugiae et Gyn. Fenniae*, vol. 62, pp. 234-239, 1973.
Broom, *J. Biomechanics*, vol. 10, pp. 707-724, 1977.

*Primary Examiner*—Maria Parrish Tungol
*Attorney, Agent, or Firm*—Fulwider, Patton, Rieber, Lee & Utecht

[57] ABSTRACT

A coating and integral treatment for improving the biophysical stability of bioprosthetic devices after implantation, particularly with respect to calcification, and, specifically, a method for treating animal tissues, such as heart valves, to provide improved biophysical stability in allograft and heterograft transplantations. The increased stability results, in-part, from the creation of a three-dimensional matrix of a primary structural component of the prosthetic device and covalently attached calcification inhibitors. Other materials, some having additional stabilizing effects, may be utilized to form additional bridges or fill the interstitial gaps in the matrix. After implantation, the resultant modified device exhibits minimal surface for intramatrix growth of calcium phosphate crystals, and additionally, may inhibit platelet aggregation, enzymatic degradation and host rejection, while minimizing the risk of mechanical failure, in the host organism.

66 Claims, No Drawings

COATING FOR BIOPROSTHETIC DEVICE AND METHOD OF MAKING SAME

BACKGROUND

For many years, a variety of animal tissues, as well as some synthetic polymers, have been used to make prosthetic devices for surgical implantation into human beings and other animals. However, because these devices are different on a molecular level from the host organism's own tissue, they usually elicit a wide variety of reactions in the host. The response is manifested by a low-grade, rapid deterioration of the transplant, which in turn, mandates additional surgery.

To improve the longevity of transplanted devices, a number of remedies have been proposed. In the processing of natural tissues, a common stabilization technique involves treatment with tanning agents, such as formaldehyde. Glutaraldehyde, a well known cross-linking agent, has also been used with success in this regard. In fact, a number of studies have shown that heart valves treated with glutaraldehyde can remain functional in situ for many years. However, recent research has indicated that such glutaraldehyde preserved implantations can still elicit significant host reactions, including calcification, fibrin deposition and an anaphylactic response. (For example, see Slanczka, D. J. and Bajpai, P. K., "Immunogenicity of Glutaraldehyde-treated Porcine Heart Valves", IRCS Medical Science: Bio-Technology; Cardiovascular System; Immunology and Allergy; Pathology; Surgery and Transplantation; 6, 421 (1978).)

It has also been theorized that natural prosthetics may be biodegradable, and thus labile even after short placement periods. In vitro enzyme degradation of the tissues prior to implantation has been utilized to minimize this obstacle, but this degradation is not totally effective in mitigating the antigenic response; and moreover, the tissue can lose significant portions of its inherent structural framework, which can cause further mechanical weakening of the entire device.

Although considerable success has been achieved by implanting synthetic devices instead of natural devices, at present, they also present significant difficulties. There is a substantial biological failure rate among these devices due to incompatibility with biological tissues. After removal of the implant, fibrin layering, aneurysm formation, lipid deposition and many clinical malfunctions have been noted.

A further problem, common to many of the synthetic and natural prosthetics alike, is minimal flexibility. Glutaraldehyde-treated natural devices are often cross-linked to such a degree that much of their natural flexibility is lost, and after prolonged periods of implantation, brittleness often becomes even more pronounced. Similarly, synthetic devices generally become increasingly hardened after prolonged implantation.

Therefore, there is a recognized need for an improved treatment of prostheic devices prior to implantation, which will render these devices more durable, yet minimize negative host responses. The present invention fulfills this need.

SUMMARY OF THE INVENTION

In accordance with one aspect of the invention, a coating for heart valves and other prosthetic devices is provided that has greatly improved biophysical stability after the device is implanted in a host organism. Through the formation of a three-dimensional cross-linked matrix primarily composed of a calcification inhibitor covalently bound to accessible regions of the device, a substantially non-antigenic bioprosthesis with minimum calcification sites may be produced.

Suitable calcification inhibitors include natural protein polysaccharides, such as chondroitin sulfates and hyaluronate. Generally, sulfated polysaccharides are preferred, but diphosphonates, phosphoproteins, dyes, such as alzarin red S and methylene blue, and other polyanions may be used.

The incorporation of other agents into the matrix can further enhance long term survival of the implanted device. Specifically, bridging agents, such as diamines, that create additional cross-linking sites and additional covalent binding sites for attaching other specified materials, such as antithrombogens, may be bound to the matrix. Also, the presence of materials that fill the interstitial gaps in the matrix can provide greater stability by limiting nucleation and the growth of hydroxyapatite crystals.

Another aspect of the invention is a process for treating bioprosthetics to provide a coating, such as described above, for improved stability after implantation. The method, which can utilize the compounds described above, comprises the steps of: havesting tissue from an organism; intitiating a number of covalent cross-links, preferably with glutaraldehyde, in the protein structure of the tissue sufficient to protect the tissue from initial losses in structural integrity; soaking the tissue in a calcification inhibitor; covalently binding the calcification inhibitor to the tissue, preferably with a carbodiimide; and sterilizing. Additional steps may include the covalent binding of bridging agents, such as diamines, antithrombogenic agents and gap filling materials to the tissue. The treatment is particularly useful for rendering animal connective tissues, such as mammalian heart valves and blood vessels, substantially water insoluble and less likely to initiate calcification than natural tissue or tanned tissue.

DETAILED DESCRIPTION OF THE INVENTION AND PREFERRED EMBODIMENTS

Exemplary starting materials useful in practicing the invention include: animal tissues of diverse origin, e.g. heart valves, blood vessels, peracardia, dura mater, ligaments, tendons, and other collagen-rich tissues, as well as reconstituted or native collagen fibers and other materials with accessible cross-linking sites. Assuming tissues are used, they are first cleaned from adherent fat or loose connective tissue as soon as possible after harvesting. Immediately thereafter, they are placed in a balanced electrolyte solution that is calcium-free and buffered at a neutral pH with a phosphate buffer. This solution kept cool (4°–8° C.), contains a calcium chelator, such as EDTA-Na at about a 0.05 molar concentration, to sequester calcium present in the tissue.

The following steps are then utilized to adequately cross-link and modify the tissue in this exemplary process:

(1) Immediately after harvesting and cleaning, the tissue is placed in a solution containing 0.05 wt.% glutaraldehyde buffered with phosphate at pH 7.0, and made isotonic with a calcium free, balanced electrolyte solution. This causes partial cross-linking of the collagen and the protein-like compounds naturally associated with it (called protein-polysacchrides) and is performed to prevent swelling and distortion of the ultrastructure of the connective tissue.

(2) The tissue is then placed in a solution containing a calcification inhibitor, preferably chondroitin sulfate at a concentration of about 0.5 to about 5 wt. %, preferably about 1.0 wt. %. Chrondroitin sulfate is available commercially or may be prepared from a variety of cartilagenous sources. In some instances, it may be desirable to use the protein-polysaccharides associated with collagen in natural tissues. These include chondroitin-6-sulfate, chondroitin-4-sulfate and hyaluronate. Generally, polysaccharides of the chondroitin sulfate variety that are rich in weak negative charges (carboxyl groups) and in strong negative charges (sulfate groups), such as sulfated polysacchrides, are preferred. Other substances that are known inhibitors of calcification include diphosphonates, which are characterized by the presence of a P-C-P or a P-N-P bond. It is theorized that P-C-P and P-N-P bonds are not "bio-degradable" and are, therefore, very stable in tissues. A typical diphosphonate is 3-amino-1-hydroxypropane 1,1-diphosphonic acid. Other diphosphonates with active amino or carboxyl groups can easily be attached by covalent bonds and act as inhibitors of calcification at the surface or within the interstitial spaces of matrices formed. Additional calcification inhibitors include phosvitin or other phosphoproteins, dyes, such as alizarin red S, and methylene blue, calcium chelators, such as EDTA and EGTA, and other polyanions. The calcium inhibitor chosen is preferably allowed to diffuse freely into the tissue, usually until equilibrium is reached, which is after about 12 hours.

(3) To the solution containing the calcium inhibitor and the tissue, an aliphatic diamine, preferably hexanediamine, is added to provide additional binding sites and cross-links in the subsequent covalent binding steps. Although diamines are preferable, other compounds with free terminal amino or carboxyl groups can be utilized. The diamine and chondroitin sulfate may be added to the solution at the same time, but by adding the calcium inhibitor first, more polyelectrolytes are probably allowed to diffuse into the tissue.

(4) The tissues and additives are then cross-linked by a water-soluble carbodiimide. Carbodiimides apparently form peptide bonds by activation of carboxyl groups to allow reaction with amino groups. The cross-linking occurs at a carbodiimide concentration of about 0.02 to about 0.1 molar, preferably about 0.05 molar, in a balanced electrolyte solution. The pH should be between about 4.7 and about 5.2, and is maintained at about 5.0 by the addition of HCl. The preferred carbodiimide is 1-ethyl-3-(3-dimethylaminopropyl)-carbodiimide HCl. If desired, ethanol and other organic solvents may be added to decrease the dielectric constant. The cross-linking reaction is allowed to proceed from about 30 minutes up to 10 hours or more.

(5) After coupling is completed, the excess reagents are removed by washing with a balanced electrolyte solution at a neutral pH, which also contains 0.05 M EDTA.

(6) The tissue is then transferred to a neutral pH buffered solution, containing about 0.2 to about 0.5 wt.% glutaraldehyde, preferably about 0.3 wt.%, in a balanced electrolyte environment. This final solution can be supplemented with alcohol at a concentration of about 20 to about 50 wt.%, and surfactants, such as anionic alkyl sulfates or alcohol and formaldehyde, for sterility and storage.

It is possible to modify the procedure stated above. For example, repeating the equilibration with the calcification inhibitor and subsequently reactivating the entire matrix with carbodiimide may be desirable.

Moreover, prior to or in conjunction with the final glutaraldehyde treatment, anti-thrombogenic compounds, such as heparin, which may also convey additional attributes, may be added at a concentration of about 0.2 to about 1.0 wt.%. Also, globular proteins, small molecular weight peptides, or poly-electrolytes, such as polylysine or polyglutamic acid, or mixed copolymers of poly-electrolytes, may be added. By allowing these materials to diffuse into the cross-linked matrix, further bridging between the tissue components and exogenous materials may occur, and the interstitial gaps may be filled. It is believed that by filling the interstitial gaps the deposit of calcium ions is minimized and hydroxyapatite and other crystal growth may be substantially inhibited.

Some basic improvements provided by the present invention will now be discussed.

I. Immunogenicity

If material implanted in an organism can be rendered insoluble, antigenicity can be substantially eliminated. To be recognized, antigens must be presented in a soluble form to activate the immune system of the host organism. In many cases, materials that are insoluble at the time of implantation can be rendered soluble by naturally occurring enzymatic or chemical processes. It is believed that the introduction of sufficient cross-links prohibits the enzyme systems of the host from solubilizing the implanted material, thereby essentially eliminating antigenicity.

Glutaraldehyde treatment also introduces cross-links, but for reasons not completely understood, the cross-links generated in the present invention render the entire device even less soluble. Without being bound to any particular reason, perhaps this reduced solubility is due to the presence of cross-links different than those created when glutaraldehyde is used alone. Since glutaraldehyde apparently acts primarily on lysine residues, the type and amount of bridges produced are somewhat limited. The present invention enhances the amount of cross-linking by covalently attaching new amino groups to the structure, and additionally allows the use of other moieties, such as peptide bound glutamic and aspartic acids, to attach more cross-links in different locations by the carbodiimide reaction mechanism.

II. Calcification

A significant, but often ignored, problem associated with the implantation of grafts rich in collagen and elastin is the propensity of these grafts to induce calcification. Collagen in particular has an intrinsic ability to calcify, and a mixture of collagen fibers with saturated solutions of calcium and phosphate ions will induce nucleation, which is closely followed by crystal growth. The addition of polyanions, particularly sulfated polysaccharides, can essentially prevent this nucleation process.

Some sulfated polysaccharides, such as endogenous chondroitin sulfate, can be bound to the collagen during the tanning procedure. But, these polyanions are usually degraded by the host and subsequently removed from the graft. Therefore, the initial protection afforded to the tissue by these materials is lost, and exposure of the functional groups in collagen, as well as the new open spaces generated, can now greatly enhance nucleation of calcium and phosphate ions. The process used in the present invention covalently links these polyanions to collagen, or some other primary structural component of the prosthetic device, and sufficiently cross-links the entire structure to prevent degradation and crystal growth. The addition of any extraneous calcification inhibitors that are also bound and cross-linked can further minimize calcification.

III. Host Induced Graft Destruction

Uncross-linked implanted, fresh heterografts or allografts are rapidly destroyed by the defense mechanisms of a host organism. Adequate cross-linking, which as previously discussed insolublizes the tissue, can prevent this destruction. Again, although glutaraldehyde induces a certain number of cross-links, these have been shown to be inadequate. Apparently, because of the different nature of the cross-links produced in the present invention, greater stability can be obtained, while the actual density of cross-links may be fewer. This is possible because the cross-links have been designed to span a broader set of distances, both inter-and intramolecular; as well as to join not only lysine residues present, but also in free carboxyl groups of glutamic and aspartic acid. Apparently, these different types of cross-links give added resistance to the treated tissues against enzymatic degradation, but importantly, without significant decreases in the mechanical attributes of the grafts.

IV. Compatibility With Blood Surfaces

Collagen, the primary structural component of most animal tissues, is a well known platelet aggregator and blood clot initiator. Since the connective tissues used in prostheses are very rich in collagen, the present invention utilizes substances capable of reducing the tissues' thrombogenic potential. Chondroitin sulfate also serves this purpose, but additional compounds with antithrombogenic properties, such as heparin, may be used. These compounds, once covalently bound, substantially decrease the ability of collagen to aggregate platelets, thereby significantly decreasing the probability of thrombus formation.

V. Changes in Mechanical Properties

The function of a transplanted device under most circumstances will depend on the retention of adequate visco-elastic behavior at a level particularly suitable for the function that the graft is to perform. Maintaining the proper amount of elasticity depends in-part on the degree of cross-linking. Insufficient cross-links could allow for flow, enzymatic degradation, and subsequent destruction of the physical integrity of the device. On the other hand, too many cross-links can be conducive to brittleness, and result in loss of function. The present invention provides an adequate number of cross-links to help retain the structural integrity of the implanted device, but not so many or so clustered that elasticity is lost.

ALTERNATIVE EMBODIMENT

Tissues are received from the slaughter house, cleaned to remove loosely adhering material, and rinsed with cold phosphate-buffered, physiological saline.

The tissues are then processed, usually at about 4° C., as follows:

(1) treat with a glutaraldehyde solution at a concentration between about 0.05 wt.% and about 0.4 wt.%, preferably about 0.15 wt.%, for between about 12 and about 64 hours, preferably about 48 hours;

(2) rinse the tissue in phosphate buffered saline to remove non-reacted glutaraldehyde;

(3) place the tissue in a solution with a pH of about 7.4 containing between about 0.1 wt.% and about 2.0 wt.% hexanediamine, preferably about 0.5 wt.%;

(4) incubate for about 2 to about 10 hours, preferably 4 hours;

(5) transfer the tissues to a buffered saline solution at a pH of about 4.9 that contains between about 0.1 and about 1.0 wt.% of a water soluble carbodiimide, preferably 0.5 wt.% 1-ethyl-3-(3-dimethylaminopropyl)-carbodiimide HCl;

(6) incubate for about 30 minutes to about 10 hours, preferably 1 hour, while maintaining the pH of the entire mixture at about pH 5.0 with an aqueous HCl solution;

(7) place the tissue in neutral, phosphate buffered saline for rinsing from about 2 to about 12 hours, preferably about 6 hours;

(8) place the tissue in a buffered neutral saline solution that contains between about 0.5 and about 3 wt.% of a sulphated polysaccharide, preferably about 1.0 wt.% chondroitin sulfate from whale and shark cartilage, the sodium salt of mixed isomers (No. C-3129, Sigma Chemical Company);

(9) incubate for about 6 to about 16 hours, preferably 12 hours, until equilibration (gentle mechanical shaking may be used);

(10) transfer the tissue to a buffered saline solution, at a pH of about 4.9 that contains about 0.1 to about 5 wt.% of a water soluble carbodiimide, preferably about 0.5 wt.% of 1-ethyl-3-(3-dimethylaminopropyl)-carbodiimide HCl, and about 0.1 to about 5 wt.% of an aliphatic diamine, preferably about 0.5 wt.% hexanediamine;

(11) incubate for about 30 minutes to about 10 hours, preferably 1 hour, while maintaining the pH of the entire mixture at about pH 5.0 with an aqueous HCl solution;

(12) rinse the tissue in a neutral, phosphate buffered saline solution from about 2 to about 12 hours, preferably about 6 hours;

(13) transfer the tissue to a neutral, phosphate buffered saline solution containing between about 0.2 and about 2.0 wt.% of an antithrombogenic agent, preferably 1.0 wt.% heparin;

(14) incubate for about 30 minutes to about 10 hours, preferably about 1 hour;

(15) add, to the solution, glutaraldehyde to a final concentration of between about 0.1 and about 1.0 wt.%, preferably about 0.4 wt.%;

(16) incubate for about 30 minutes to about 10 hours, preferably about 1 hour;

(17) transfer to a final storage, neutral, phosphate buffered solution containing about 0.4 wt.% glutaraldehyde, preferably about 0.4 wt.%, about 0.2 to about 2.0 wt.% of formaldehyde, preferably about 1.0 wt.% and about 20 to about 40 wt.% alcohol, preferably about 30 wt.%.

Although the invention has been described in detail, it will be understood by one of ordinary skill in the art that various modifications can be made without departing from the spirit and scope of the invention. Accordingly, it is not intended that the invention be limited except as by the appended claims.

We claim:

1. A process for improving the biophysical stability of bioprostheses for heterograft or allograft implantation, which comprises:
   harvesting tissue from an organism;
   initiating covalent cross-links in the protein structure of the tissue to protect the tissue from excessive swelling or other losses of structural integrity;
   soaking the tissue in an aqueous solution of a calcification inhibitor;
   covalently binding the calcification inhibitor to the tissue thereby forming a three-dimensional matrix; and
   sterilizing the matrix;
   wherein the modified tissue produced is substantially water insoluble; and, after implantation in a host organism, the matrix is less likely to elicit an antigenic response or to be subject to calcification than natural tissue or tanned tissue.

2. The process of claim 1 wherein the calcification inhibitor is a polyanion.

3. The process of claim 1 wherein the calcification inhibitor is an anionic polysaccharide.

4. The process of claim 1 wherein the calcification inhibitor is a sulphated polysaccharide.

5. The process of claim 1 wherein the calcification inhibitor is selected from the group consisting of chondroitin-4-sulfate, chondroitin-6-sulfate, hyaluronate and mixtures thereof.

6. The process of claim 1 wherein the intiation of cross-links is made by reacting the tissue with glutaraldehyde.

7. The process of claim 1 wherein the covalent binding of the calcification inhibitor is made by reacting the tissue with a water soluble carbodiimide.

8. The process of claim 7 wherein the carbodiimide is 1-ethyl-3-(3-dimethylaminopropyl)-carbodiimide HCl.

9. The process of claim 1 wherein the matrix is sterilized in a solution containing formaldehyde, alcohol or mixtures thereof.

10. The process of claim 1 wherein the aqueous solution used during the tissue soaking also contains a bridging agent that will covalently bind to the tissue during the covalent binding step; thereby providing additional sites for peptide bond formation and additional structural stability to the matrix.

11. The process of claim 10 wherein the bridging agent is a diamine.

12. The process of claim 11 wherein the diamine is an aliphatic diamine.

13. The process of claim 1 further including: soaking the tissue in the presence of a bridging agent.

14. The process of claim 13 wherein the bridging agent is covalently bound to the modified tissue to provide additional sites for covalent bond formation.

15. The process of claim 13 wherein the bridging agent is a diamine.

16. The process of claim 15 wherein the diamine is an aliphatic diamine.

17. The process of claim 1 further including:
   covalently bonding an antithrombogenic agent to the matrix.

18. The process of claim 17 wherein the antithrombogenic agent is heparin.

19. The process of claim 1 further including: soaking the tissue in the presence of materials that fill the interstitial gaps of the matrix.

20. The process of claim 19 wherein the gap filling material is covalently bound to the matrix during subsequent covalent bonding steps.

21. The process of claim 19 wherein the gap filling material is a protein.

22. The process of claim 21 wherein the protein is a globular protein.

23. The process of claim 19 wherein the gap filling material is a polyelectrolyte.

24. The process of claim 23 wherein the polyelectrolyte is polylysine, polyglutamic acid, copolymers of polylysine and polyglutamic acid or mixtures thereof.

25. The process of claim 1 further including: forming additional covalent cross-links in the three-dimensional matrix.

26. The process of claim 25 wherein the forming of the additional cross-links is made by reacting the three-dimensional matrix with glutaraldehyde.

27. The process of claim 1 wherein the tissue is an animal connective tissue.

28. The process of claim 27 wherein the animal connective tissue is a mammalian heart valve, blood vessel, percardium, dura mater, ligament, tendon or other collagen-rich tissue.

29. The process of claim 1 wherein the step of initiating covalent cross-links in the protein structure is performed before the step of soaking the tissue in an aqueous solution of a calcification inhibitor.

30. A bioprosthetic device made according to the process of any one of claims 1–5 or 6–28.

31. A coating for a prosthetic device that provides increased stability for allograft or heterograft implantations, said coating comprising:
   a three dimensional, cross-linked matrix of an exogenous calcification inhibitor covalently bound to accessible regions of the device wherein the coating is substantially non-antigenic and has minimal calcification initiation sites.

32. The coating of claim 31 wherein the calcification inhibitor is a polyanion.

33. The coating of claim 31 wherein the calcification inhibitor is a sulphated polysaccharide.

34. The coating of claim 38 wherein the calcification inhibitor is a protein-polysaccharide.

35. The coating of claim 34 wherein the protein-polysaccharide is chondroitin-4-sulfate, chondroitin-6-sulfate, hyaluronate or mixtures thereof.

36. The coating of claim 31 wherein the matrix also contains an exogenous, covalently bond, antithrombogenic agent.

37. The coating of claim 36 wherein the antithrombogenic agent is heparin.

38. The coating of claim 31 wherein the matrix also contains a covalently bound bridging agent to provide additional binding sites for the exogenous reagents and to provide structural integrity to the matrix through additional cross-links.

39. The coating of claim 38 wherein the bridging agent is a diamine.

40. The coating of claim 39 wherein the diamine is an aliphatic diamine.

41. The coating of claim 31 wherein a material is covalently bound to the matrix that fills the interstitial spaces of the matrix.

42. The coating of claim 41 wherein the gap filling material is a protein.

43. The coating of claim 42 wherein the protein is a globular protein.

44. The coating of claim 41 wherein the gap filling material is a polyelectrolyte.

45. The coating of claim 44 wherein the polyelectrolyte is polylysine, polyglutamic acid, copolymers of polysine and polyglutamic acid or mixtures thereof.

46. A process for treating heart valves prior to implantation into a human comprising the steps of:
 harvesting a fresh heart valve from a donor organism;
 initiating cross-links in the valve by treating with glutaraldehyde;
 incubating the valve in a solution containing a diamine;
 reacting the valve with a water soluble carbodiimide;
 soaking the valve in a solution containing a sulphated polysaccharide;
 reacting the valve with a water soluble carbodiimide in the presence of a diamine;
 soaking the valve in a solution containing heparin;
 reacting the valve with glutaraldehyde;
 storing the valve in a sterilizing solution.

47. A prosthesic heart valve suitable for implantation into a human comprising:
 a chondroitin sulfate, hexanediamine and heparin covalently attached to a mammalian heart valve through carbodiimide and glutaraldehyde induced bonds, wherein the device is substantially cross-linked and possesses viscoelastic properties similar to natural heart valves.

48. A process for improving the biophysical stability of bioprotheses for heterograft or allograft implantation, which comprises:
 harvesting tissue from an organism;
 initiating covalent cross-links in the protein structure of the tissue to protect the tissue from excessive swelling or other losses of structural integrity;
 soaking the tissue in an aqueous solution of a diphosphonate.
 covalently binding the diphosphonate to the tissue thereby forming a three-dimensional matrix; and
 sterilizing the matrix;
 wherein the modified tissue produced is substantially water insoluble; and, after implantation in a host organism, the matrix is less likely to elicit an antigenic response or to be subject to calcification than natural tissue or tanned tissue.

49. The process of claim 48 wherein the diphosphonate is 3-amino-1-hydroxypropane 1, diphosphonic acid.

50. A process for improving the biophysical stability of bioprostheses for heterograft or allograft implantation, which comprises:
 harvesting tissue from an organism;
 initiating covalent cross-links in the protein structure of the tissue to protect the tissue from excessive swelling or other losses of structural integrity;
 soaking the tissue in an aqueous solution of a dye;
 covalently binding the dye to the tissue thereby forming a three-dimensional matrix; and
 sterilizing the matrix;
 wherein the modified tissue produced is substantially water insoluble; and, after implantation in a host organism, the matrix is less likely to elicit an antigenic response or to be subject to calcification than natural tissue or tanned tissue.

51. The process of claim 50 wherein the dye is alizarin red S, methylene blue or mixtures thereof.

52. A process for improving the biophysical stability of bioprostheses for heterograft or allograft implantation, which comprises:
 harvesting tissue from an organism;
 initiating covalent cross-links in the protein structure of the tissue to protect the tissue from excessive swelling or other losses of structural integrity;
 soaking the tissue in an aqueous solution of a phosphoprotein;
 covalently binding the phosphoprotein to the tissue thereby forming a three-dimensional matrix; and
 sterilizing the matrix;
 wherein the modified tissue produced is substantially water insoluble; and, after implantation in a host organism, the matrix is less likely to elicit an antigenic response or to be subject to calcification than natural tissue or tanned tissue.

53. The process of claim 52 wherein the phosphoprotein is phosvitin.

54. A process for improving the biophysical stability of bioprostheses for heterograft or allograft implantation, which comprises:
 harvesting tissue from an organism;
 initiating covalent cross-links in the protein structure of the tissue to protect the tissue from excessive swelling or other losses of structural integrity;
 soaking the tissue in an aqueous solution of a chelating agent;
 covalently binding the chelating agent to the tissue thereby forming a three-dimensional matrix; and
 sterilizing the matrix;
 wherein the modified tissue produced is substantially water insoluble; and, after implantation in a host organism, the matrix is less likely to elicit an antigenic response or to be subject to calcification than natural tissue or tanned tissue.

55. The process of claim 54 wherein the chelating agent is EDTA or EGTA.

56. A coating for a prosthetic device that provides increased stability for allograft or heterograft implantations, said coating comprising;
 a three dimensional, cross-linked matrix of an exogenuous diphosphonate covalently bound to accessible regions of the device wherein the coating is substantially non-antigenic and has minimal calcification initiation sites.

57. The coating of claim 56 wherein the diphosphonate is 3-amino-1-hydroxypropane 1, 1-disphosphonic acid.

58. A coating for a prosthetic device that provides increased stability for allograft or heterograft implantation, said coating comprising;
 a three dimensional, cross-linked matrix of an exogenuous dye covalently bound to accessible regions of the device wherein the coating is substantially non-antigenic and has minimal calcification initiation sites.

59. The coating of claim 58 wherein the dye is alizarin red S, methylene blue or mixtures thereof.

60. A coating for a prosthetic device that provides increased stability for allograft or heterograft implantations, said coating comprising;
 a three dimensional, cross-linked matrix of an exogenuous phosphoprotein covalently bound to accessible regions of the device wherein the coating is substantially non-antigenic and has minimal calcification initiation sites.

61. The coating of claim 60 wherein the phosphoprotein is phosvitin.

62. A coating for a prosthetic device that provides increased stability for allograft or heterograft implantations, said coating comprising:
 a three dimensional, cross-linked matrix of an exogenuous chelating agent covalently bound to accessible regions of the device wherein the coating is substantially non-antigenic and has minimal calcification initiation sites.

63. The coating of claim 62 wherein the chelating agent is EDTA or EGTA.

64. A process for improving the biophysical stability of bioprostheses for heterograft or allograft implantation, which comprises:
 harvesting tissue from an organism;
 initiating covalent cross-links in the protein structure of the tissue to protect the tissue from excessive swelling or other losses of structural integrity;
 soaking the tissue in an aqueous solution of chondroitin sulfate; and
 soaking the tissue in an aqueous solution of a water-soluble carbodiimide;
 wherein chondroitin sulfate is covalently bonded to the tissue and the tissue produced is substantially water insoluble; and, after implantation in a host organism, the matrix is less likely to elicit an antigenic response or to be subject to calcification than natural tissue or tanned tissue.

65. The process of claim 64 wherein the tissue is soaked in a water-soluble carbodiimide before it is soaked in chondroitin sulfate.

66. The process of claim 64 wherein the water-soluble carbodiimide is 1-ethyl-3-(3-dimethylaminopropyl)-carbodiimide HCl.

* * * * *